US010391200B2

(12) United States Patent
Gho

(10) Patent No.: US 10,391,200 B2
(45) Date of Patent: Aug. 27, 2019

(54) METHOD FOR IN VIVO HAIR MULTIPLICATION

(71) Applicant: Hair Science Institute, Amsterdam (NL)

(72) Inventor: Conradus Ghosal Gho, Bunde (NL)

(73) Assignee: HAIR SCIENCE INSTITUTE, Amsterdam (NL)

( * ) Notice: Subject to any disclaimer, the term of this patent is extended or adjusted under 35 U.S.C. 154(b) by 351 days.

(21) Appl. No.: 14/650,883

(22) PCT Filed: Dec. 12, 2013

(86) PCT No.: PCT/NL2013/050891
§ 371 (c)(1),
(2) Date: Jun. 10, 2015

(87) PCT Pub. No.: WO2014/092571
PCT Pub. Date: Jun. 19, 2014

(65) Prior Publication Data
US 2015/0314044 A1 Nov. 5, 2015

(30) Foreign Application Priority Data
Dec. 12, 2012 (NL) ...................................... 2009971

(51) Int. Cl.
*A61K 8/58* (2006.01)
*A61K 8/60* (2006.01)
*A61K 8/66* (2006.01)
*A61K 8/98* (2006.01)
*A61Q 7/00* (2006.01)
*A61L 27/36* (2006.01)
*A61L 27/38* (2006.01)
*C12N 5/071* (2010.01)

(52) U.S. Cl.
CPC ............ *A61L 27/3691* (2013.01); *A61K 8/58* (2013.01); *A61K 8/602* (2013.01); *A61K 8/66* (2013.01); *A61K 8/983* (2013.01); *A61L 27/3604* (2013.01); *A61L 27/3641* (2013.01); *A61L 27/38* (2013.01); *A61L 27/3804* (2013.01); *A61L 27/3895* (2013.01); *A61Q 7/00* (2013.01); *C12N 5/0627* (2013.01); *C12N 5/0628* (2013.01); *A61K 2800/591* (2013.01); *A61L 2430/18* (2013.01); *A61L 2430/40* (2013.01); *C12N 2502/115* (2013.01)

(58) Field of Classification Search
None
See application file for complete search history.

(56) References Cited

U.S. PATENT DOCUMENTS

| 6,399,057 | B1* | 6/2002 | Gho | A61K 8/985 424/70.1 |
| 2007/0128172 | A1* | 6/2007 | Yoshizato | A61F 2/10 424/93.7 |
| 2010/0034856 | A1* | 2/2010 | Gho | A61K 8/985 424/401 |
| 2011/0130711 | A1* | 6/2011 | Lederman | A61B 18/203 604/22 |
| 2013/0096600 | A1* | 4/2013 | Wesley | A61F 2/10 606/187 |
| 2014/0079686 | A1* | 3/2014 | Barman | A61K 8/4953 424/94.67 |

FOREIGN PATENT DOCUMENTS

| EP | 0236014 A1 | 9/1987 |
| EP | 0971679 B1 | 6/2002 |
| EP | 1957092 B1 | 8/2012 |
| WO | 2005/077285 A1 | 8/2005 |
| WO | 2007/061291 A2 | 5/2007 |
| WO | 2007/109223 A2 | 9/2007 |

OTHER PUBLICATIONS

Gho-JDT, Gho et al., Donor hair follicle preservation by partial follicular unit extraction. A method to optimize hair transplantation, Journal of Dermatological Treatment. 2010; Early Online, 1-13.*
Parsley et al., Review of factors affecting the growth and survival of follicular grafts, Journal of Cutaneous and Aesthetic Surgery, 2010, vol. 3, Issue 2, p. 69-75.*
Perez et al., The use of autologous platelet rich and platelet poor plasma to enhance the wound healing and hair growth in hair restoration, 13th Annual Scientific Meeting, International Society of Hair Restoration Surgery, 2005.*
Kempson, et al., "A Method for the Longitudinal Sectioning of Single Hair Samples", J. Forensic Sci., vol. 47, No. 4, 2002.

* cited by examiner

*Primary Examiner* — Taeyoon Kim
*Assistant Examiner* — Srikanth Patury
(74) *Attorney, Agent, or Firm* — Hoffmann & Baron, LLP

(57) ABSTRACT

Cosmetic methods providing a significant improvement over existing hair transplantation methods by providing greater hair density per hair implant, which is achieved through the process of an enhanced hair multiplication in vivo (e.g. in the scalp of a subject). The cosmetic methods also provide improved aesthetic results, particularly, more realistic and natural looking results, relative to the results obtained by traditional methods. The cosmetic methods are particularly suitable for hair transplantation in recipient areas of a subject experiencing baldness or lack of hair, optionally due to Androgenic alopecia, burn injuries, cancer chemotherapy, or other genetic or environmental factors or scarring.

15 Claims, No Drawings

METHOD FOR IN VIVO HAIR MULTIPLICATION

CROSS-REFERENCE TO RELATED APPLICATIONS

This application is the National Stage of International Application No. PCT/NL2013/050891 filed Dec. 12, 2013, which claims the benefit of Netherlands Application No. 2009971, filed Dec. 12, 2012, the contents of which is incorporated by reference herein.

FIELD OF THE INVENTION

The present invention is in the field of cosmetic and aesthetic procedures, specifically in the field of hair multiplication technology. The present invention particularly relates to improved cosmetic methods for in vivo hair multiplication that can be used to overcome baldness. The cosmetic method of the present invention is particularly suitable for hair transplantation in recipient areas of a subject experiencing baldness or lack of hair, optionally due to Androgenic alopecia, burn injuries, cancer chemotherapy, or other genetic or environmental factors or scarring.

BACKGROUND OF THE INVENTION

Baldness is the partial or complete lack of hair in certain areas of the body, mostly the head. The degree and pattern of baldness can vary greatly among individuals. The most common cause of hair loss and hair thinning in humans is male pattern baldness also referred to as Androgenic alopecia. Variant forms of Androgenic alopecia also exist in both men and women. Androgenic alopecia and variants thereof are not life threatening conditions but they often cause mental stress. Androgenic alopecia also occurs in animals such as in chimpanzee and orangutans. In humans, this condition is characterized by hair lost in a well-defined pattern, beginning above both temples. Hair also thins at the crown of the head, eventually causing this area to become partially or completely bald, leaving only a rim of hair around the sides and rear of the head. Baldness occurs more frequently in men and is especially more prevalent with advancing age. Baldness is less frequently observed in women. Although classic male pattern baldness or Androgenic alopecia rarely occurs in women, other variants of this condition where the hair becomes thinner around the whole scalp, but without the hairline receding, are observed in women.

Overall, baldness is considered undesirable from a cosmetic and aesthetic standpoint for both men and women. Therefore, considerable efforts have been devoted to combat baldness including, for instance, therapies aimed at lowering stress (cortisol) levels, hormonal therapy (e.g. 5α-reductase inhibitors), immunosuppressant therapy, and cosmetic procedures, such as hair transplant procedures.

Early hair transplant procedures consisted of removing hairs from a donor region covered with hair and transplanting donor hairs in a bald area. One of the donor areas often chosen for such procedure is the back of the head since hairs growing in this region are usually insensitive to Androgenic alopecia and variants thereof or other forms of baldness. During such procedures, donor hair along with a relatively large part of the skin surrounding the donor hair is harvested, and then transplanted in a suitable recipient area. Although the transplanted hairs settle relatively well at the transplant area and eventually become permanent with normal growth cycle, such method is far from being optimal. Specifically, one of the major disadvantages of this method is that not only the hairs removed from the donor region will never grow again but also the esthetic results obtained after hair transplant are disappointing for lack of realistic appearance. That is because of the relatively large size of the graft (hair plugs) requiring large puncture size for receiving the graft, and the poor hair density per hair implant. Furthermore, the issues related to the low hair density achieved by these method is difficult to counteract since only a limited amount of hair transplant (hair plugs) can be performed during a given surgical procedure. In sum, such hair transplantation technique offers very limited possibilities and is not "patient-friendly".

Different hair transplant techniques have also been developed in an effort to improve the issues discussed above, and include methods for in vitro reproduction of hair or hair cloning. Such methods exploit the characteristics of the hair follicle. The essential growth structures of hair are the hair follicles, which contain hair follicular stem cells responsible for the growth of a new hair. The hair follicles also produce hair follicle cells or keratinocytes. During their journey to the surface of the skin, the cytoplasm of the hair follicle cells undergoes a large number of complex processes, which ultimately lead to the production of the tough and elastic material known as hair. The growth cycle of hair can be subdivided into three phases including the anagen phase ('growth phase'), the catagen phase ('transitional phase'), and the telogen phase ('death phase'). The hair follicle plays a unique role in the cyclic nature of hair formation and hair growth, since it is the only part of the body that has the ability to completely regenerate (i.e. produce a new hair) after its removal from the body. This knowledge has been tested in vitro where it has been shown that hair follicle cells from plucked human hair can be cultured outside the body. It is also known that it is possible to use such cultured cells to form a differentiated epidermis or a fully developed epidermis, both in vitro and in vivo. Cultured hair follicle cells from mice can stimulate hair growth when said cells are implanted into test animals.

A hair transplant method exploiting this concept has been disclosed in European Patent Application 0236 014, in which epidermal follicle cells of the desired hair type are removed from the scalp skin of a donor subject. The epidermal follicle cells are then cultured in a culture medium, which preferably contains growth factors. In a subsequent step, a opening is made in the epidermis of the patients scalp and, via said opening, the cultured epidermal follicle cells are introduced/injected into the dermis next to the epidermis. Although an improvement over the more crude hair transplant method discussed above, the disadvantage of this method is that it is a very invasive procedure and that epidermal follicle cells cannot easily be placed in a targeted manner (i.e. to achieve a specific growth direction) on the scalp or other facial areas. In addition to that, the probability that the injected epidermal follicle cells will regenerate into the recipient region is rather low and as a result, large amount of epidermal follicle cells are required to increase the likelihood of survival. This represents an important limiting factor since such cells are not easily obtained and are difficult to culture in vitro.

Another hair transplantation method relying on the concept of hair multiplication has been described in European patent application 0 971 679. In this method, the donor hair in the anagen phase is removed from a donor area in such a way that the growth of a new hair (to replace the plucked hair), is enabled in the donor area. This method can be used to produce a new hair from the hair follicle stem cells obtained from the harvested hair. However, for this technique to succeed, the hair follicle stem cells must be cultured for long periods (ranging from 1 hour to 40 days, in a serum-free keratinocyte culture medium) before the donor hair can be implanted in the recipient area and produce a new hair. Therefore a main disadvantage of this method is the long time needed for culturing the hair follicle stem cells, causing inconveniency to the recipient subject, who must return to the clinic frequently in order to finalize the procedure. This is costly, time-consuming, and not "patient-friendly". A refinement of this method has been described in European patent application 1957092. Although the time needed for culturing the hair follicle stem cells was greatly shorten, the esthetic results obtained still remain suboptimal since only a low density of hair can be achieved per hair transplant unit, i.e. only one new hair can be produced from the implanted donor hair (1 to 2 gain).

However, there is still a great need for improved hair transplantation methods relying on the concept of hair multiplication but where the aesthetic results obtained are more realistic and more natural looking. This may be achieved by increasing hair density per hair transplant unit in the recipient area. It is a goal of the present invention to provide an improved in vivo hair multiplication method, particularly to increase the hair density per hair transplant unit.

SUMMARY OF THE INVENTION

In a first aspect, the present invention relates to a cosmetic method for in vivo hair multiplication, comprising the steps of:
(a) providing at least a part of a hair follicle in the anagen phase, said at least a part of a hair follicle comprising at least one hair follicular stem cell; and
(b) making at least one incision along the longitudinal axis of said at least a part of a hair follicle; and
(c) contacting said at least a part of a hair follicle of step (b) with a medium for at least 1 second.

In a second aspect, the present invention relates to a cosmetic method for in vivo hair multiplication in a subject, comprising the steps of:
(a1) optionally, administering to said subject a composition comprising at least one anti-apoptotic compound and at least one anti-oxidant compound; and
(b1) removing at least a part of a hair follicle in the anagen phase from said subject, said at least a part of a hair follicle comprising at least one hair follicular stem cell; and
(c1) making at least one incision along the longitudinal axis of said at least a part of a hair follicle; and
(d1) contacting said at least a part of a hair follicle of step (c) with a medium for at least 1 second; and
(e1) implanting said at least a part of a hair follicle of step (d) into a recipient area of said subject; and
(f1) optionally, administering to said subject a composition comprising at least one anti-apoptotic compound and at least one anti-oxidant compound.

In an embodiment, the cosmetic methods of the invention further comprise, preferably after steps (a) and/or (b1), more preferably after steps (a) and/or (b1) and prior to steps (b) and/or (c1), the step of: longitudinally sectioning the at least a part of a hair follicle to produce at least two of said at least a part of a hair follicle, each of the two of said at least a part of a hair follicle comprising at least one hair follicular stem cell.

In an embodiment, said anti-apoptotic compound of step (a1) and step (f1) is a physiologically acceptable vanadium compound, preferably Bis (maltolato) oxovanadium.

In an embodiment, said anti-oxidant compound of step (a1) and step (f1) is mono-hydroxyethyl rutoside.

In another embodiment, the composition of step (a1) is administered daily for at least 14 days before step (b1).

In a further embodiment, the composition of step (f1) is administered daily for at 14 days after step (d1).

In an embodiment, said at least a part of a hair follicle in the anagen phase of steps (a) and/or (b1) has been obtained by plucking the hair from a donor area of a subject.

In another embodiment, said medium of steps (c) and/or (d1) is selected from a medium comprising platelet rich plasma, platelet poor plasma, an activator compound, an anti-oxidant compound, and an anti-apoptotic compound; and a medium comprising extracellular matrix.

In an embodiment, said activator compound is thrombin.

In an embodiment, said anti-oxidant compound is quercetin, and/or vitamin C, and/or vitamin E.

In an embodiment, the anti-apoptotic compounds is selected from the group of: a physiologically acceptable vanadium compounds and insulin growth factor.

In another embodiment, said physiologically acceptable vanadium compound is preferably Bis (maltolato) oxovanadium.

In another embodiment, said medium of steps (c) and/or (d1) is in the form of a gel or semi-liquid paste.

In an embodiment of the present invention, said at least a part of a hair follicle and/or longitudinally sectioned at least a part of a hair follicle in the anagen phase of steps (a) and/or (b1) is derived from a subject, and the medium of steps (c) and/or (d1) comprises platelet rich plasma, and/or platelet poor plasma and/or serum derived from said subject.

In an embodiment, said donor hair is obtained from one or more donor areas insensitive to Androgenic alopecia, and wherein said donor areas are preferably located in the lower back of the head.

In another embodiment, at least a part of the hair follicle remains in the donor subject, and wherein said at least part of the hair follicle is capable of regenerating a hair.

In an aspect of the present invention, the at least a part of hair follicle and/or longitudinally sectioned at least a part of hair follicle obtained in steps (c) and/or (d1), is suitable for implantation into the skin.

In an embodiment, the at least a part of hair follicle and/or longitudinally sectioned at least a part of hair follicle obtained in steps (c) and/or step (d1), is implanted into the top layers of the skin, i.e. the epidermis and dermis, e.g., at least 0.1 mm but no more than 4 mm from the external surface of the skin. The skilled person will readily be able to determine the correct depth of implantation depending on the implantation site.

In another embodiment, the at least a part of hair follicle and/or longitudinally sectioned at least a part of hair follicle obtained in steps (c) and/or (d1), is suitable for performing hair transplant in head areas such as scalp, eyebrows, beard, and moustache.

In a further embodiment, the at least a part of hair follicle and/or longitudinally sectioned at least a part of hair follicle obtained in steps (c) and/or (d1) is suitable for performing hair transplant to cover a scar, or for performing hair transplant in a subject experiencing hair loss due to Androgenic alopecia or variants thereof or other forms of baldness cause by genetic or environmental factors, or for performing hair transplant in a subject experiencing hair loss due to a burn injury, or for performing hair transplant in a subject experiencing hair loss due to cancer chemotherapy.

DETAILED DESCRIPTION OF THE INVENTION

General Definition

The term "hair follicle" refers to a mammalian skin organ that produces hair. More particularly, the hair follicle is composed of the dermal papilla (DP), dermal sheath (DS), outer root sheath (ORS), inner root sheath (IRS), and hair shaft. The ORS contains "hair follicular stem cells", which are the cells giving rise to the production of a new hair during the anagen phase of the hair cycle. The upper and lower parts of the hair follicle both comprise hair follicular stem cells that are capable of generating a new hair. These are referred to as 'bulge stem cells' and 'matrix stem cells', respectively.

The term "at least a part of a hair follicle" as used herein refers to a part of a single hair follicle or an entire hair follicle. The at least a part of a hair follicle comprises at least one hair follicular stem cell, but preferably more than one. The hair follicular stem cells may be either bulge stem cells or matrix stem cells, or both. Preferably, the hair follicular stem cells comprise at least bulge stem cells or derivatives thereof. Preferably the at least a part of a hair follicle comprises at least a part of a hair to facilitate growth of a hair in a desired direction. As used herein, the term "at least a part of a hair follicle" may also refer to a longitudinally sectioned at least a part of a hair follicle.

The terms "anagen phase", "catagen phase", and "telogen phase" represent the three phases of the natural growth cycle of the hair, including the growth phase, the transitional phase (also referred to as involuting or regressing phase), and the death phase (also referred to as resting or quiescent phase), respectively.

The terms "hair multiplication" refers to a situation where the presence of multiple divided hair matrices and papillae, gives rise to the formation of multiple hair shafts within the individual follicles.

The term "Androgenic alopecia" refers to a condition cited as the most common cause of hair loss and thinning in humans. A variety of genetic (and possibly environmental) factors have been proposed to play a role in androgenic alopecia. For instance, genetic sensitivity of the hair follicles to dihydrotestosterone (DHT) has been identified as an important factor since DHT causes hair follicles to shrink or miniaturize, which in turn shortens their lifespan and prevents them from producing hair normally.

The term "three dimensional culture" refers to a method of culturing cells wherein cells are implanted or seeded into an artificial structure capable of supporting three-dimensional tissue formation. These structures, typically called scaffolds, are critical, both ex vivo as well as in vivo, to recapitulating the in vivo milieu and allowing cells to influence their own microenvironments.

The term "extracellular matrix component" is a term well known to those skilled person. Substitutes thereof are also known in the art. Non-limiting examples of extracellular matrix component are collagen, laminin, elastin, fibronectin, and the like.

Cosmetic Methods of the Invention

In a first aspect, the present invention relates to a cosmetic method for in vivo hair multiplication, comprising the steps of:

(a) providing at least a part of a hair follicle in the anagen phase, said at least a part of a hair follicle comprising at least one hair follicular stem cell; and (b) making at least one incision along the longitudinal axis of said at least a part of a hair follicle; and (c) contacting said at least a part of a hair follicle of step (b) with a medium for at least 1 second.

In a second aspect, the present invention relates to a cosmetic method for in vivo hair multiplication in a subject, comprising the steps of:

(a1) optionally, administering to said subject a composition comprising at least one anti-apoptotic compound and at least one anti-oxidant compound; and (b1) providing at least a part of a hair follicle in the anagen phase from said subject, said at least a part of a hair follicle comprising at least one hair follicular stem cell; and (c1) making at least one incision along the longitudinal axis of said at least a part of a hair follicle; and (d1) contacting said at least a part of a hair follicle of step (c1) with a medium for at least 1 second; and (e1) implanting said at least a part of a hair follicle of step (d1) into a recipient area of said subject; and (f1) optionally, administering to said subject a composition comprising at least one anti-apoptotic compound and at least one anti-oxidant compound.

In an embodiment, the at least a part of a hair follicle is longitudinally sectioned to produce at least two of said at least a part of a hair follicle, each of the two of said at least a part of a hair follicle comprising at least one hair follicular stem cell. This step preferably takes place after steps (a) and/or (b1), more preferably after steps (a) and/or (b1) and prior to steps (b) and/or (c1). Methods for longitudinally sectioning the at least part of a hair follicle into at least two of said at least a part of a hair follicle are known in the art. For example, one can use a sharp and thin razorblade. For other techniques that may be employed, see, e.g., Kempson et al. (J Forensic Sci, July 2002, Vol. 47, No. 4:1-4).

Overall, it was found by the present inventor that the cosmetic methods described herein are associated with significantly enhanced in vivo hair multiplication relative to what has been achieved previously with existing hair multiplication methods. Specifically, it was unexpectedly found that when the at least a part of a hair follicle and/or the longitudinally sectioned at least a part of a hair follicle was incised along its longitudinal axis prior to implantation, the implant settled well and up to 10 new hairs may be generated from the single (optionally longitudinally sectioned) at least a part of a hair follicle.

In addition, the methods of the present invention offers other great advantages over the existing hair multiplication methods, including greater hair density per transplant unit as well as improved aesthetic results, i.e. the achievement of more realistic and natural looking results. This is achievable because the methods of the present invention not only provides greater hair density per hair implant in the recipient area (e.g. scalp) but also allow the natural regrowth of the plucked hair in the donor area, which guarantees no hair density loss in the donor region of a subject. Furthermore, because the perforations (i.e. punctures made by the plucking and implanting needle) made to harvest and implant donor hairs are very small (pore size <1 mm), both harvest and implant locations are undistinguishable from the surrounding (unprocessed) areas. As a result, hair grafts can be placed much more tightly together, in a manner that mimic natural hair arrangement, so as to avoid undesirable (unnatural looking) effects such as "bunching effects".

In steps (a) and/or (b1) of the methods of the present invention, the provision of at least a part of a hair follicle in the anagen phase can be performed by any methods known in the art, e.g. plucking one or more donor hairs from a donor subject, such as the scalp of a donor subject, and then selecting one or more donor hairs in the anagen phase. Selecting a donor hair in the anagen phase can be performed by a person with ordinary skill in the art. It is well known that a hair in the anagen phase displays specific morphological and histological characteristics that distinguish it from a hair in another phase of the growth cycle, such as the catagen phase or telogen phase. For instance, a donor hair in the anagen phase displays a pigmented bulb due to the presence of melamine pigments whereas a hair either in the catagen phase or telogen phase displays a very scarce amount of pigments or no pigment at all, respectively. Another difference is the presence of root sheaths, which are abundant in a hair in the anagen phase but which are practically absent in a hair in the catagen phase or telogen phase.

The hair may be plucked using any methods known in the art. For examples, the hair may be plucked using fingers or a plucking instrument (e.g. tweezers) may be used. In a embodiment, the donor hair is removed using a plucking instrument such as a hollow harvesting needle, as described in WO2005/077285.

In an embodiment, the at least a part of a hair follicle and/or longitudinally sectioned at least a part of a hair follicle of steps (a) and/or (b1) can be obtained from one or more donor areas of a subject. A donor area is preferably insensitive to Androgenic alopecia. Said donor area may, for example, be located in the lower back of the head. It is well known that the lower back of the head is often insensitive to Androgenic alopecia and other forms of baldness.

In an embodiment, a donor hair is plucked from one or more donor areas of a donor subject in such a way that said at least a part of a hair follicle, preferably at least the upper part of a hair follicle, remains attached to the plucked hair. The (optionally longitudinally sectioned) at least a part of a hair follicle comprises at least one hair follicular stem cell, preferably at least one bulge stem cell. Preferably, the at least a part of a hair follicle (which is optionally longitudinally sectioned) comprises several hair follicular stem cells. For example, the (optionally longitudinally sectioned) at least a part of a hair follicle may comprise at least a part of the pool of bulge stem cells, preferably at least part of the upper pool of bulge stem cells. In an embodiment, the at least a part of a hair follicle comprises at least 2, 5, 8, 10, 15, 20, 30, 40, 50, 100, 200, 500, 1000 or more hair follicular stem cells.

In steps (b) and/or (c1) of the method of the present invention, at least one incision along the longitudinal axis of the (optionally longitudinally sectioned) at least a part of a hair follicle is made. In an embodiment, at least 2, 3, 4, 5, 6, 7, 8, or even 10 incisions are made along the (optionally longitudinally sectioned) longitudinal axis of the at least a part of a hair follicle. This is accomplished by using a sharp knife or a sharp scalpel or a sharp razor blade or any sharp cutting instruments known in the art, many of which are commercially available. The at least one incision may be made superficially from the outer surface of the (optionally longitudinally sectioned) at least a part of a hair follicle so that it does not transect the at least a part of a hair follicle. The at least one incision can be made anywhere along the outer surface of the (optionally longitudinally sectioned) at least a part of a hair follicle. Incisions on the hair shaft per se, where no hair follicle material, is present should be avoided. The angle of the incision is not important for the cosmetic method of the invention so long as the at least one incision is performed along the longitudinal axis of the (optionally longitudinally sectioned) at least a part of a hair follicle. Remarkably, the present inventor has unexpectedly found that the number of incisions positively correlates with the number of new hairs generated, i.e., as more incisions are made, more new hairs are formed from the (optionally longitudinally sectioned) at least a part of a hair follicle.

Prior to making said at least one incision along the longitudinal axis of the (optionally longitudinally sectioned) at least a part of a hair follicle, said (optionally longitudinally sectioned) at least a part of a hair follicle may optionally be contacted with a composition comprising activated, preferably autologous, platelet rich plasma. The activation of said platelet rich plasma has preferably been carried out using thrombin.

It may be advantageous to administer a pre-treatment to the donor subject before providing, e.g., by plucking, one or more hairs from said donor subject. Said pre-treatment may be orally administered to the donor subject in the form of a composition comprising at least one anti-apoptotic compound and at least one anti-oxidant compound. Specifically, the present inventor has shown that pre-treating a donor subject may be advantageous to improve the condition of the at least a part of a hair follicle and/or the longitudinally sectioned at least a part of a hair follicle by improving its quality and promote its growth prior to its removal, e.g., from the scalp of the subject. Pre-treatment of a donor subject with a composition comprising at least one anti-apoptotic compound and at least one anti-oxidant compound may also be advantageous to promote a faster healing process by preventing or reducing apoptosis and oxidative damage. Furthermore, pre-treatment of the donor subject with a composition comprising at least one anti-apoptotic compound and at least one anti-oxidant compound may also be advantageous to minimize the chances of scarring after removing the at least a part of a hair follicle in the anagen phase and/or the longitudinally sectioned at least a part of a hair follicle in the anagen phase from said subject, a procedure that may create small wounds (i.e. puncture holes created by the plucking needle) in the donor areas.

Anti-apoptotic compounds and anti-oxidant compounds are known in the art and can be obtained from commercial suppliers. In one embodiment of the invention, the anti-apoptotic compound and the anti-oxidant compound of the pre-treatment composition of step (a1) may be obtained from a commercial supplier. In a preferred embodiment, the pre-treatment composition contains an anti-apoptotic compound such as Bis(maltolato)-oxovanadium and an anti-oxidant compound such as mono-hydroxyethyl rutoside.

In an embodiment of the invention, the composition of step (a1) is administered daily for at least 14 days before step (b1). Preferably, said composition is ingested by said subject once a day for at least 14 days prior to step (b1). The composition may be in any form, preferably suitable for ingestion, such as tablet, capsule, drink, and the like.

When bis(maltolato)oxovanadium is used, it may be administered in an effective amount. An effective amount of bis(maltolato)oxovanadium may be between 0.003 mg and 3 g, such as between 0.03 and 300 mg, such as between 0.3 and 30 mg, such as between 1 and 10 mg, e.g., about 3 mg.

When mono-hydroxyethyl rutoside is used, it may be administered in an effective amount. An effective amount of mono-hydroxyethyl rutoside may be between 5 mg and 50 g, such as between 50 and 5000 mg, such as between 100 and 1000 mg, such as between 250 and 750 mg, e.g., about 500 mg.

In steps (c) or (d1) of the method of the present invention, the at least a part of a hair follicle of steps (b) or (c1) and/or a longitudinally sectioned at least a part of a hair follicle of step (b) or (c1) is contacted with a medium for at least one second. For example, the at least a part of a hair follicle and/or a longitudinally sectioned at least a part of a hair follicle may be immersed in said medium. According to the method of the present invention, it is not necessary to culture the at least a part of a hair follicle and/or the longitudinally sectioned at least a part of a hair follicle of steps (b) or (c1). A brief immersion or contact lasting at least 1 second between the at least a part of a hair follicle and/or the longitudinally sectioned at least a part of a hair follicle of steps (b) or (c1) with the medium of steps (c) or (d1) is sufficient for generating at least one or more new hairs from the at least a part of a hair follicle and/or the longitudinally sectioned at least a part of a hair follicle of steps (b) or (c1). However, longer immersion or contact (>2 seconds) between the at least a part of a hair follicle and/or the longitudinally sectioned at least a part of a hair follicle of steps (b) or (c1) with the medium of steps (c) or (d1) is possible but not necessary according to the method of the present invention. The at least a part of a hair follicle of steps (b) or (c1) and/or a longitudinally sectioned at least a part of a hair follicle of steps (b) or (c1) may be contacted with a medium for any length of time, however, in an embodiment the time of contact between the at least a part of a hair follicle and/or a longitudinally sectioned at least a part of a hair follicle and the medium is less than 24 hours, such as less than 20, 16, 12, 8, 7, 6, 5, 4, 3, 2, 1 hour, or less than 50, 40, 30, 20, 10, 9, 8, 7, 6, 5, 4, 3, 2, or 1 minute, or less than 50, 50, 30, 20, 10, 9, 8, 7, 6, 5, 4, 3, or 2 seconds.

The medium used may be any medium known in the art for the propagation of hair, such as a medium comprising extracellular matrix components or substitutes thereof (see, e.g., WO2007/061291). For example, commercially available medium comprising extracellular matrix compound can be employed in the method of the present invention. Protocols and recipes for making medium comprising extracellular matrix components are also well known in the art.

Alternatively, the medium may comprise platelet rich plasma, which is preferably activated, e.g., using thrombin. The medium may further comprise one or more anti-oxidant compounds and/or one or more anti-apoptotic compounds. In an embodiment, the at least a part of a hair follicle of steps (b) or (c1) and/or a longitudinally sectioned at least a part of a hair follicle of steps (b) or (c1) is placed in between a solution or hydrogel comprising non-activated platelet rich plasma and a solution or hydrogel comprising activated thrombin. In a suitable embodiment, the platelet rich plasma and/or activated thrombin is autologous, i.e. is derived from the subject to be implanted with the at least a part of a hair follicle and/or a longitudinally sectioned at least a part of a hair follicle.

The medium may be in the form of a gel, e.g., a hydrogel, or semi-liquid paste.

In an embodiment, the medium of steps (c) or (d1) may further comprise at least one of the following ingredients selected from the group of: an anti-apoptotic compound, an anti-oxidant compound, and a stem cell enhancer compound. Any commercially available anti-apoptotic compounds, anti-oxidant compounds, and stem cell enhancer compounds can be used in the cosmetic methods of the present invention. However, in an embodiment of the invention, the anti-apoptotic compound in the medium of steps (c) or (d1) is a physiologically acceptable vanadium compound and/or insulin growth factor. In an embodiment, the physiologically acceptable anti-apoptotic compound is Bis(maltolato)oxovanadium. The anti-oxidant compound in the medium of steps (c) or (d1) may be quercetin, and/or vitamin C, and/or vitamin E. The stem cell enhancer compound in the medium of steps (c) or (d1) may be retinoid acid and/or erythropoietin.

In an embodiment of the invention, the at least a part of a hair follicle and/or longitudinally sectioned at least a part of a hair follicle of steps (b) or (c1) can be further cultured. Any method known in the art may be used for culturing the at least a part of a hair follicle and/or longitudinally sectioned at least a part of a hair follicle, particular hair follicular stem cells, such as bulge cells. The use of three-dimensional cell culture system may be particularly advantageous for culturing and growing the at least a part of a hair follicle (containing at least one hair follicular stem cell) and/or longitudinally sectioned at least a part of a hair follicle (containing at least one hair follicular stem cell). It is known that three-dimensional cell culture systems allow various types of interactions to occur between the different cell types present in the culture in a manner that mimics what occurs in a natural environment. Methods for performing three-dimensional cell culture are also well known in the art.

In a further embodiment of the invention, it is not necessary that the at least a part of a hair follicle and/or the longitudinally sectioned at least a part of a hair follicle of steps (b) or (c1) be wholly contacted with, e.g., immersed in, the medium of steps (c) or (d1). Selectively contacting, e.g., immersing, only the part of the at least part of a hair follicle which contains at least one hair follicular stem cell and/or selectively contacting, e.g., immersing, only the part of the longitudinally sectioned at least part of a hair follicle which contains at least one hair follicular stem cell attached of steps (b) or (c1), is sufficient for generating or multiplying at least one new hair or more, in vivo, using the cosmetic methods according to the present invention.

In step (e1), the at least a part of a hair follicle and/or longitudinally sectioned at least a part of a hair follicle of step (d1) may be implanted in one or more recipient areas in a recipient subject. In an embodiment, the recipient subject is the same as the donor subject. In one embodiment, the at least a part of a hair follicle and/or longitudinally sectioned at least a part of a hair follicle of step (d1) is implanted in one or more recipient areas using an implanting needle such as a hollow implanting needle, as described in patent application WO2005/077285. In a further embodiment, the at least a part of a hair follicle and/or longitudinally sectioned at least a part of a hair follicle of step (d1) is implanted into the upper layers of skin of a subject, i.e. epidermis and dermis, e.g., at least 0.1 mm but no more than 4 mm from the surface of the skin. In a preferred embodiment of the invention, the at least a part of a hair follicle and/or longitudinally sectioned at least a part of a hair follicle of step (d1) is implanted into the skin of the head areas such as scalp, eyebrows, beard, and moustache.

In step (f1), it may be advantageous to administer a post-treatment to the donor and/or recipient subjects after removing or implanting one or more hairs from said donor or recipient subject, respectively. Said post-treatment may be orally administered to the donor and/or recipient subject in the form of a composition comprising at least one anti-apoptotic compounds and at least one anti-oxidant compounds. Specifically, the present inventor has shown that post-treating a donor subject may be advantageous to improve the regrowth and condition of the new hair, which replaces the plucked hair in the donor region. Similarly, the present inventor has shown that post-treating a recipient subject may be advantageous to improve the condition of the at least a part of a hair follicle and/or the longitudinally sectioned at least a part of a hair follicle obtained in steps (c) or (d1), by improving its quality and promote its growth after its implantation in a recipient area in a recipient subject. Post-treatment of a donor and/or recipient subject with a composition comprising at least one anti-apoptotic compound and at least one anti-oxidant compound may also be advantageous to promote a faster healing process by preventing or reducing apoptosis and oxidative damage. Furthermore, post-treatment of the donor and/or recipient subject with a composition comprising at least one anti-apoptotic compound and at least one anti-oxidant compound may also be advantageous to minimize the chances of scarring after removing or implanting the at least a part of a hair follicle in the anagen phase and/or the longitudinally sectioned at least a part of a hair follicle in the anagen phase from said donor or recipient subject, respectively.

Anti-apoptotic compounds and anti-oxidant compounds are known in the art and can be obtained from commercial suppliers. In one embodiment of the invention, the anti-apoptotic compound and the anti-oxidant compound of the pre-treatment composition of step (f1) may be obtained from a commercial supplier. In a preferred embodiment, the pre-treatment composition contains an anti-apoptotic compound such as Bis (maltolato) oxovanadium and an anti-oxidant compound such as mono-hydroxyethyl rutoside. In another embodiment of the invention, the composition of step (f1) is administered daily for at least 14 days after step (f1). Preferably, said composition is ingested by said subject once a day for at least 14 days after step (f1). The composition may be in any form, preferably suitable for ingestion, such as tablet, capsule, drink, and the like.

When bis(maltolato)oxovanadium is used, it may be administered in an effective amount. An effective amount of bis(maltolato)oxovanadium may be between 0.003 mg and 3 g, such as between 0.03 and 300 mg, such as between 0.3 and 30 mg, such as between 1 and 10 mg, e.g., about 3 mg.

When mono-hydroxyethyl rutoside is used, it may be administered in an effective amount. An effective amount of mono-hydroxyethyl rutoside may be between 5 mg and 50 g, such as between 50 and 5000 mg, such as between 100 and 1000 mg, such as between 250 and 750 mg, e.g., about 500 mg.

In is also a goal of the present invention to provide improved cosmetic methods for in vivo hair multiplication that are not detrimental to the donor area.

In a preferred embodiment, the invention provides cosmetic methods for in vivo hair multiplication, wherein at least a part of the hair follicle containing at least one hair follicular stem cell, remains in one or more of the donor hair follicular areas upon removal by plucking, and wherein said at least one hair follicular stem cell is capable of regenerating a new hair in one or more donor hair follicular areas after removing or plucking of the at least a part of the hair follicle. Therefore, the method of the present invention is not detrimental or disadvantageous for the donor area, since hair can regrow normally in the donor area after removal or plucking. Methods to remove at least a part of a hair follicle in such a manner that a small portion of the hair follicle containing at least one hair follicular stem cell remains in the dermis upon plucking are known in the art and have, for example, been described in patent applications WO2005/077285 and WO2007/061291.

Suitable uses of the cosmetic methods of the present invention

The cosmetic methods and composition of the present invention may be suitable for performing hair transplant, e.g., to cover a scar, or in a subject experiencing hair loss due to Androgenic alopecia or variants thereof or other forms of baldness cause by genetic or environmental factors, or in a subject experiencing hair loss due to a burn injury, or in a subject experiencing hair loss due to cancer chemotherapy.

EXAMPLE 1

Induced-hair Multiplication from Hair Follicular Stem Cells

Material

Whole blood from a subject was collected in a citrate anticoagulant (ACD-A) in a 7:1 ratio (seven parts whole blood to one part citrate anticoagulant). The whole blood was gently mixed with the citrate anticoagulant.

Autologous platelet rich plasma (PRP) was prepared from the whole blood using routine methods. Similarly, platelet poor plasma was prepared from the whole blood. Autologous thrombin serum was produced from the platelet poor plasma using the activAT System (Cytomedix Inc., Gaithersburg, USA). 10 mL concentrated preservative medium as provided in the activAT kit was added to 10 mL autologous thrombin serum to obtain 20 mL enriched activated thrombin. Subsequently, 5 mL enriched activated thrombin was added to 5 mL autologous PRP to obtain 10 mL autologous activated PRP.

A total of 10 hairs were plucked from a donor area from a subject. The plucked hairs were stored in autologous activated PRP. Subsequently, the plucked hairs were incised 4 times along the longitudinal axis. The incised hairs were then covered and impregnated with autologous hydrogel of PRP and enriched activated thrombin which resulted in incised hairs covered in autologous activated PRP. The 10 hairs were subsequently implanted in a recipient area of said subject. It was found that about 3-5 new hairs were formed per implanted plucked and incised hair. It was also found that at the donor area from which the hairs were plucked, new hairs grew.

In a parallel experiment, the same experimental procedure was repeated, except that the 10 plucked hairs were incised 7 times along their longitudinal axis. The 10 hairs were then subsequently implanted in a recipient area of said subject. It was found that about 7-10 new hairs were generated per implanted plucked and incised hair. It was also found that at the donor area from which the hairs were plucked, new hairs grew.

The invention claimed is:

1. A cosmetic method for in vivo hair multiplication, comprising the steps of:
  (a) harvesting at least a part of a hair follicle in the anagen phase, said at least a part of a hair follicle comprising at least one hair follicular stem cell;
  (b) after said harvesting, making at least two incisions along the longitudinal axis of said at least a part of a hair follicle;
  (c) contacting said at least a part of a hair follicle of step (b) with a medium for at least 1 second; and
  (d) implanting said at least a part of a hair follicle of step (c) into a recipient area of a subject;

wherein the incisions avoid the hair shaft per se, where no hair follicle material is present.

2. The cosmetic method according to claim 1, wherein the at least a part of a hair follicle in the anagen phase has been obtained by plucking the hair from a donor area of a subject.

3. The cosmetic method of claim 1, wherein the medium is selected from a medium comprising platelet rich plasma, platelet poor plasma, thrombin, an anti-oxidant compound, and an anti-apoptotic compound; and a medium comprising extracellular matrix.

4. The cosmetic method according to claim 3, wherein the anti-oxidant compound is quercetin, and/or vitamin C, and/or vitamin E.

5. The cosmetic method according to claim 3, wherein the anti-apoptotic compounds is selected from the group of: a physiologically acceptable vanadium compounds and insulin growth factor.

6. The cosmetic method according to claim 5, wherein physiologically acceptable vanadium compound is bis(maltolato)oxovanadium.

7. The cosmetic method according to claim 1, wherein the medium is in the form of a gel or semi-liquid paste.

8. The cosmetic method according to claim 1, wherein at least a part of a hair follicle in the anagen phase is derived from a subject, and the medium comprises platelet rich plasma, and/or platelet poor plasma and/or serum derived from said subject.

9. The cosmetic method according to claim 1, wherein the donor hair is obtained from one or more donor areas insensitive to Androgenic alopecia, and wherein said donor areas are preferably located in the lower back of the head.

10. The cosmetic method according to claim 8, wherein at least a part of the hair follicle remains in the subject, and wherein said at least part of the hair follicle is capable of regenerating a hair.

11. The cosmetic method according to claim 1, wherein the at least a part of hair follicle obtained in step (c), is suitable for implantation into the skin.

12. The cosmetic method according to claim 1, wherein the at least a part of hair follicle obtained in step (c), is implanted into the upper layers of the skin at least 0.1 mm but no more than 4 mm from the external surface of the skin.

13. The cosmetic method according to claim 12, wherein the upper layers of the skin comprise epidermis and dermis.

14. The cosmetic method according to claim 1, wherein the at least a part of hair follicle obtained in step (c), is suitable for performing hair transplant in head areas selected from scalp, eyebrows, beard, and moustache.

15. The cosmetic method according to claim 1, wherein the at least a part of hair follicle obtained in step (c), is suitable for performing hair transplant to cover a scar, or for performing hair transplant in a subject experiencing hair loss due to Androgenic alopecia or variants thereof or other forms of baldness cause by genetic or environmental factors, or for performing hair transplant in a subject experiencing hair loss due to a burn injury, or for performing hair transplant in a subject experiencing hair loss due to cancer chemotherapy.

* * * * *